US010401295B2

(12) United States Patent
Jena et al.

(10) Patent No.: US 10,401,295 B2
(45) Date of Patent: Sep. 3, 2019

(54) COMPOSITION AND METHOD FOR MONITORING LIPID (71) Applicant: Memorial Sloan-Kettering Cancer Center, New York, NY (US)

(72) Inventors: Prakrit Jena, New York, NY (US); Daniel A. Heller, New York, NY (US); Daniel Roxbury, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 27 days.

(21) Appl. No.: 15/313,580

(22) PCT Filed: May 28, 2015

(86) PCT No.: PCT/US2015/032891
§ 371 (c)(1),
(2) Date: Nov. 23, 2016

(87) PCT Pub. No.: WO2015/184096
PCT Pub. Date: Dec. 3, 2015

(65) Prior Publication Data
US 2017/0199126 A1 Jul. 13, 2017

Related U.S. Application Data (60) Provisional application No. 62/004,122, filed on May 28, 2014.

(51) Int. Cl.
*B82Y 5/00* (2011.01)
*B82Y 15/00* (2011.01)
(Continued)

(52) U.S. Cl.
CPC ....... *G01N 21/6489* (2013.01); *A61B 5/1455* (2013.01); *A61B 5/14546* (2013.01);
(Continued)

(58) Field of Classification Search
None
See application file for complete search history.

(56) References Cited

U.S. PATENT DOCUMENTS

| 4,930,516 A | 6/1990 | Alfano et al. |
| 2004/0171099 A1 | 9/2004 | Cali et al. |

(Continued)

FOREIGN PATENT DOCUMENTS

| WO | WO-2011/081884 A1 | 7/2011 |
| WO | WO-2015/184096 A1 | 12/2015 |
| WO | WO-2015/184096 A8 | 12/2016 |

OTHER PUBLICATIONS

Amiot et al., "Near-infrared fluorescent materials for sensing of biological targets," Sensors, vol. 8, No. 1, pp. 3082-3105 (Jan. 1, 2008).

(Continued)

*Primary Examiner* — Neil N Turk
(74) *Attorney, Agent, or Firm* — Foley & Lardner LLP (57) ABSTRACT

A method of detecting a condition in a subject comprises the steps of contacting cells of the subject with single-walled carbon nanotubes (SWCNTs), monitoring photoluminescence emitted by SWCNTs internalized into the cells and generating an SWCNT emission profile, comparing the SWCNT emission profile to a control emission profile for the SWCNTs to produce a result, and determining a likelihood of having the condition in the subject based on the result from the comparing step. Also disclosed is a method for screening agents capable of changing endocytic environment using SWCNTs.

1 Claim, 6 Drawing Sheets

(51) Int. Cl.
*B82Y 30/00* (2011.01)
*A61B 5/145* (2006.01)
*G01N 21/64* (2006.01)
*A61B 5/1455* (2006.01)
*G01N 33/53* (2006.01)

(52) U.S. Cl.
CPC .............. *B82Y 5/00* (2013.01); *B82Y 15/00* (2013.01); *B82Y 30/00* (2013.01); *G01N 21/6486* (2013.01); *G01N 21/6428* (2013.01)

(56) References Cited

U.S. PATENT DOCUMENTS

| | | | | |
|---|---|---|---|---|
| 2008/0297022 | A1* | 12/2008 | Maruyama | B82Y 30/00 313/309 |
| 2011/0045523 | A1 | 2/2011 | Strano et al. | |
| 2011/0195522 | A1 | 8/2011 | Clarke et al. | |
| 2011/0204258 | A1 | 8/2011 | Heller et al. | |
| 2011/0269243 | A1* | 11/2011 | Strano | B82Y 30/00 436/172 |
| 2012/0003278 | A1 | 1/2012 | Kirkpatrick et al. | |
| 2013/0035567 | A1 | 2/2013 | Strano et al. | |
| 2013/0259807 | A1 | 10/2013 | Bissell et al. | |
| 2014/0079635 | A1 | 3/2014 | Wang | |

OTHER PUBLICATIONS

Bertulli et al., "Spectroscopic characteristics and cellular compatibility of protein wrapped single wall carbon nanotubes," 2012 IEEE International Conference on Nanotechnology, pp. 1-5 (Aug. 20, 2012).
Heller, et al., "Single-walled carbon nanotubes spectroscopy in live cells: towards long-term labels and optical sensors," Advanced Materials, vol. 17, No. 23, pp. 2793-2799 (Dec. 5, 2005).
Huang et al., "Near-infrared fluorescence spectroscopy of single-walled carbon nanotubes and its applications," Trac Trends in Analytical Chemistry, vol. 30, No. 7, pp. 1109-1119 (Jul. 1, 2011).
Leeuw et al., "Single-walled carbon nanotubes in the intact organism: near-IR imaging and biocompatibility studies in *drosophilia*," Nano Letters, American Chemical Society, vol. 7, No. 9, pp. 2650-2654 (Sep. 1, 2007).
Wang et al., "SWCNT PEG-eggs: single-walled carbon nanotubes in biocompatible shell-crosslinked micelles," Carbon, vol. 45, No. 12, pp. 2388-2393 (Sep. 21, 2007).
Arnold, M.S. et al., Sorting carbon nanotubes by electronic structure using density differentiation, Nature Nanotechnology, 1:60-65 (2006).
Bachilo, S.M. et al., Narrow (n,m)-Distribution of Single-Walled Carbon Nanotubes Grown Using a Solid Supported Catalyst, J. Am. Chem. Soc., 125:11186-11187 (2003).
Bachilo, S.M. et al., Structure-Assigned Optical Spectra of Single-Walled Carbon Nanotubes, Science, 298(5602):2361-2366 (2002).
Barone, P.W. et al., Near-infrared optical sensors based on single-walled carbon nanotubes, Nature Materials, 4:86-92 (2005).
Bayer, N. et al., Effect of Bafilomycin A1 and Nocodazole on Endocytic Transport in HeLa Cells: Implications for Viral Uncoating and Infection, Journal of Virology, 72(12):9645-9655 (1998).
Bhattacharya, S. et al., DNA Conjugated SWCNTs Enter Endothelial Cells via Rac1 Mediated Macropinocytosis, Nano Lett., 12:1826-1830 (2012).
Caldwell, J.D. et al., Experimental evidence for mobile luminescence center mobility on partial dislocations in 4H-SiC using hyperspectral electroluminescence imaging, Applied Physics Letters, 102:242109, 5 pages,(2013).
Chang, C. I., Hyperspectral Data Processing: Algorithm Design and Analysis, John Wiley & Sons, Inc., First Edition, 30 pages, (2013).
Chang, T.Y. et al., Niemann-Pick Type C Disease and Intracellular Cholesterol Trafficking, Journal of Biological Chemistry, 280:20917-20920 (2005).

Cherukuri, P. et al., Near-Infrared Fluorescence Microscopy of Single-Walled Carbon Nanotubes in Phagocytic Cells, J. Am. Chem. Soc., 126:15638-15639 (2004).
Choi, J.H. and Strano, M.S., Solvatochromism in single-walled carbon nanotubes, Applied Physics Letters, 90:223114, 4 pages, (2007).
Cognet, L. et al., Stepwise Quenching of Exciton Fluorescence in Carbon Nanotubes by Single-Molecule Reactions, Science, 316(5830):1465-1468 (2007).
Davidson, C.D. et al., Chronic Cyclodextrin Treatment of Murine Niemann-Pick C Disease Ameliorates Neuronal Cholesterol and Glycosphingolipid Storage and Disease Progression, PLoS ONE, 4(9):e6951, 15 pages, (2009).
Delamarre, A. et al., Contactless mapping of saturation currents of solar cells by photoluminescence, Applied Physical Letters, 100:131108, 4 pages (2012).
Efimov, O.M. et al., High-efficiency Bragg gratings in photothermorefractive glass, Applied Optics, 38(4):619-627 (1999).
Grabinksi, C. et al., Hyperspectral Microscopy for Characterization of Gold Nanoparticles in Biological Media and Cells for Toxicity Assessment, Methods in Molecular Biology, 1025:167-178 (2013).
Haraguchi, T. et al., Spectral imaging fluorescence microscopy, Genes to Cells, 7(9):881-887 (2002).
Heller, D.A. et al., Optical Detection of DNA Conformational Polymorphism on Single-Walled Carbon Nanotubes, Science, 311(5760):508-511 (2006).
Huotari, J. and Helenius, A., Focus Review—Endosome maturation, The EMBO Journal, 30(17):3481-3500 (2011).
International Search Report, PCT/US2015/032891, 3 pages, dated Aug. 14, 2015.
Jin, H. et al., Single-Particle Tracking of Endocytosis and Exocytosis of Single-Walled Carbon Nanotubes in NIH-3T3 Cells, Nano Letters, 8(6):1577-1585 (2008).
Kim, J.H. et al., The rational design of nitric oxide selectivity in single-walled carbon nanotube near-infrared fluorescence sensors for biological detection, Nature Publishing Group, 1(6):473-481 (2009).
Koh, C.H.V. and Cheung, N.S., Cellular mechanism of U18666A-mediated apoptosis in cultured murine cortical neurons: Bridging Niemann-Pick disease type C and Alzheimer's disease, 18:1844-1853 (2006).
Leavesley, S.J. et al., HyperSpectral imaging microscopy for identification and quantitative analysis of fluorescently-labeled cells in highly autofluorescent tissue, J Biophotonics, 5(1):67-84 (2012).
Lefebvre, J. et al., Photoluminescence from an individual single-walled carbon nanotube, Physical Review B, 69:075403-1-075403-5 (2004).
Lefebvre, J. et al., Photoluminescence Imaging of Suspended Single-Walled Carbon Nanotubes, Nano Letters, 6(8):1603-1608 (2006).
Liu, H. et al., Large-scale single-chirality separation of single-wall carbon nanotubes by simple gel chromatography, Nature Communications, 2:309:1-8 (2011).
Mendes De Oliveira, C. et al., The Brazilian Tunable Filter Imager for the SOAR Telescope, The Astronomical Society of the Pacific, 125:396-408 (2013).
Mukherjee, S. et al., Endocytosis, Physiological Reviews, 77(3):759-803 (1997).
O'Connel, M.J. et al., Band Gap Fluorescence from Individual Single-Walled Carbon Nanotubes, Science, 297(5581):593-596 (2002).
Pipalia, N.H. et al., Histone deacetylase inhibitor treatment dramatically reduces cholesterol accumulation in Niemann-Pick type C1 mutant human fibroblasts, PNAS, 108(14):5620-5625 (2011).
Rosenbaum, A.I. et al., Endocytosis of beta-cyclodextrins is responsible for cholesterol reduction in Niemann-Pick type C mutant cells, PNAS, 107(12):5477-5482 (2010).
Seber, G. A. F., Multivariate Distributions, Multivariate Observations, John Wiley & Sons, Inc., Chapter 2, pp. 17-58 (2004).
Tsyboulski, D.A. et al., Structure-Dependent Fluorescence Efficiencies of Individual Single-Walled Carbon Nanotubes, Nano Letters, 7(10):3080-3085 (2007).
Tu, X. et al., DNA sequence motifs for structure-specific recognition and separation of carbon nanotubes, Nature Letters, 460:250-253 (2009).

(56) References Cited

OTHER PUBLICATIONS

Van Der Meer, F.D. et al., Multi- and hyperspectral geologic remote sensing: A review, International Journal of Applied Earth Observation and Geoinformation, 14:112-128 (2012).

Vered et al., Fluorescence-based diagnosis of lipid storage disease of analysis of the culture medium of skin fibroblasts, Clinica Chimica Acta. 218(2):139-147 (1993) [retrieved on Jul. 29, 2015], retrieved from the Internet. <URL:ttp://www.ncbi.nim.nih.gov/pubmed/8306439>, abstract.

Welsher, K. et al., Deep-tissue anatomical imaging of mice using carbon nanotube fluorophores in the second near-infrared window, PNAS, 108(22):8943-8948 (2011).

Written Opinion, PCT/US2015/032891, 9 pages, dated Aug. 14, 2015.

Yang, R. et al., Carbon Nanotube-Quenched Fluorescent Oligonucleotides: Probes that Fluoresce upon Hybridization, J. Am. Chem. Soc., 130:8351-8358 (2008).

Choi et al., "Multimodal biomedical imaging with asymmetric single-walled carbon nanotube/iron oxide nanoparticle complexes," Nano Letters, vol. 7, No. 4, pp. 861-867 (Mar. 3, 2017).

\* cited by examiner

FIGURE 6

COMPOSITION AND METHOD FOR MONITORING LIPID

CROSS-REFERENCE TO PRIOR APPLICATIONS

This application is a U.S. National Stage Entry of International PCT Application No.: PCT/US15/32891, filed May 28, 2015, which claims priority to U.S. Provisional Application No. 62/004,122, filed May 28, 2014, the contents of each of which are incorporated herein in their entireties.

This invention was made with government support under grant number HD075698 awarded by the National Institutes of Health. The government has certain rights in the invention.

FIELD

The present disclosure relates generally to devices and methods for monitoring lipid and, in particular, lipid in a biological sample or intracellular lipid using carbon nanotube-based optical reporters.

BACKGROUND

Lysosomes are vacuolar organelles responsible for the breakdown of lipids, proteins, sugars, and other cellular material into their constituent components. To degrade intracellular organelles, lysosomes fuse with autophagosomes to form autolysosomes, while extracellular cargo marked for further processing and degradation is directed to the lysosome from the endolysosomal pathway itself. In addition, lysosomes are involved in nutrient sensing of engulfed amino acids. During starvation, mTORC1 is inhibited and autophagy is induced, thus indicating lysosomes as a link between nutrient availability and signaling pathways related to cell growth.

A growing body of work implicates lysosomal dysfunction in a range of pathologies. Dysfunction in the ability of lysosomes to catabolize or export their contents results in lysosomal storage disorders, a family of diseases characterized by pathologies caused by the accumulation of undigested substrates. Lysosomal cholesterol accumulation is causal during inflammation in both atherosclerosis and non-alcoholic steatohepatitis. Defects in the fusion of lysosomes with autophagosomes leads to an accumulation of autolysosomes in the neurons of patients with amyotrophic lateral sclerosis (ALS), while impaired autolysosomal proteolysis is implicated in both Alzheimer's and Parkinson's diseases. The ability to observe changes in the lipid content of lysosomes is crucial to understanding the distinct roles played by the lysosomes in such a variety of diseases. However, no one has developed and/or applied imaging or any other method to observe endogenous cholesterol and/or other lipids in live cells and animals. It would be advantageous to do so for a number of reasons including, for example, to measure and detect cholesterol and other lipids in early stage disease detection.

Spectral imaging is a powerful tool for detection, validation, separation, and quantification in applications ranging from mineral assessment of geological satellite images to semiconductor material characterization. In contrast to multi-spectral imaging in discrete wavelength bands, hyperspectral imaging produces a full, quasi-continuous emission spectrum at every spatial pixel. Several methods exist for hyperspectral data acquisition, including pixel-by-pixel, line-by-line acquisition of spectra, or globally by acquiring separate images at each wavelength. Recent applications of global hyperspectral imaging have used volume Bragg gratings (VBG) to acquire spectrally-defined images from the scanned wavelength space, for the mapping of solar cell saturation currents and in astronomical imaging.

SUMMARY

One aspect of the application relates to a method of detecting a condition in a subject using single-walled carbon nanotubes (SWCNTs). The method comprises the steps of contacting cells of a subject with SWCNTs, monitoring photoluminescence emitted by SWCNTs internalized into the cells and generating an SWCNT emission profile, comparing the SWCNT emission profile to a control emission profile for the SWCNTs, and determining a likelihood of having the condition in the subject based on a result from the comparing step.

Another aspect of the application relates to a method for screening agents capable of changing endocytic dielectric environment. The method comprises the steps of contacting testing cells with a candidate agent, wherein the testing cells contain internalized SWCNTs, monitoring photoluminescence emitted by internalized SWCNTs and generating a SWCNT emission profile, and comparing the SWCNT emission profile to a control emission profile for the SWCNTs to produce a result, wherein the candidate agent is an agent that is capable of changing endocytic dielectric environment if the result shows a significant difference between the SWCNT emission profile to a control emission profile.

Another aspect of the application relates to a method for measuring lipid content in a sample. The method comprises the steps of mixing the sample with SWCNTs, monitoring photoluminescence emitted by the SWCNTs and generating a sample SWCNT emission profile, comparing the sample SWCNT emission profile to a control SWCNT emission profile or emission value, and determining a lipid content in the sample based on the result of said comparing step.

In some embodiments, the SWCNTs are semi-conductive SWCNTs. In other embodiments, the SWCNTs are polymer-coated non-covalently encapsulated SWCNTs. In other embodiments, the SWCNTs are encapsulated by DNA oligonucleotides, wherein the DNA oligonucleotides are $ss(GT)_6$ oligonucleotides. In other embodiments, the SWCNTs have chiral indices (n,m) of (6,5) or (8,6). In other embodiments, the SWCNTs are $ss(GT)_6$ (8,6) SWCNTs.

In some embodiments, the SWCNT emission profile detected is a solvatochromatic response which indicates that photoliuminescence emitted by SWCNTs is blue-shifted, wherein the blue-shifted emission indicates substantial lipid (such as cholesterol) accumulation in the local dielectric environment.

In some embodiments, the condition is a disease linked to elevated lipid or cholesterol content. In other embodiments, the condition is a lysosomal storage disorder selected from the group consisting of Niemann-Pick, Tay-Sachs and Gaucher's disease. In another embodiment, the condition is hypercholesterolemia. In another embodiment, the condition is a disease selected from the group consisting of atherosclerosis, coronary heart diseases, stroke, diabetes, fatty liver disease and cancer. In another embodiment, the cells contacted with SWCNTs are cultured in vitro. In another embodiment, the cells contacted with SWCNTs are located in a subject in vivo.

In another embodiment, the cells contacted with SWCNTs are cells extracted from the subject. The method further comprises the steps of: extracting cells from the subject;

incubating the extracted cells with SWCNTs; and monitoring a wavelength-shifted solvatochromatic response of the SWCNTs. In some embodiments, the wavelength-shifted solvatochromatic response is a blue-shifted emission by the SWCNTs. In some embodiments, the cells are fibroblast cells. In other embodiments, the cells are microphages. In other embodiments, the cells are hepatocytes. In other embodiments, the cells are cancer cells. In other embodiments, the cells are lymphocytes or blood cells.

The SWCNTs function as a carbon nanotube optical reporter (CNOR) via solvatochromic shifting of its emission in response to a change in the immediate dielectric environment, allowing solvatochromic measurements which are free of artifacts induced by photobleaching, concentration, and movement of the emitter through the optical field. When applied to live cells, the CNOR wavelength transiently and reversibly reflected the changing dielectric environment of the maturing endosome. In some embodiments, the CNOR measures a drug-induced increase in endosomal cholesterol or lipid via an enhanced blue-shift and is capable of identifying the high free cholesterol or lipid content in human patient fibroblasts with the NPC1 mutation and benchmarked disease-state reversal on treatment with cyclodextrin. Applications of the CNOR using hyperspectral imaging will allow new functional measurements of analytes in living systems for the study of disease, drug screening and clinical applications.

BRIEF DESCRIPTION OF THE DRAWINGS

The accompanying drawings illustrate one or more embodiments of the present disclosure and, together with the written description, serve to explain the principles of the exemplary embodiments of the present disclosure.

FIG. 1 illustrates various aspects of reporter response to lipidic molecules. Panel A illustrates normalized absorption and emission spectra of the ss(GT)$_6$-encapsulated (8,6) SWCNTs; Panel B illustrates response of the emission wavelength of surface-adsorbed ssGT$_6$-(8,6) SWCNTs to solvent dielectric (error bar is from triplicate technical replicates); Panel C illustrates emission wavelength of ssGT$_6$-(8,6) SWCNTs in solution as a function of added LDL concentration; Panel D illustrates overly of transmitted light image and hyperspectral image of the reporter in RAW 264.7 cells incubated in LPDS, and in LPDS with Ac-LDL and U18666A added (color legend maps to nanotube emission peak); Panel E illustrates histogram from the combined emission from ss(GT)$_6$-(8,6) SWCNTs under the two conditions previously listed; Panel F illustrates MD simulation 5 image of ss(GT)$_6$-(8,6) SWCNTs in water, and in the presence of additional cholesterol molecules; Panel G illustrates water density on the nanotube surface for ss(GT)$_6$-(8,6) SWCNTs, and in the presence of added cholesterol.

FIG. 2 illustrates various aspects of an exemplary SWCNT solvatochromic response to endosomal dielectric environment. Panel A is an illustration of exemplary time-course histograms of ss(GT)$_6$-encapsulated (8,6) SWCNTs emission from live HeLa cells showing that at 30 minutes, a narrow distribution of emission wavelengths was observed, centered at 1200.7±0.4 nm and after 6 hours of incubation, SWCNTs in the majority of endosomes were blue-shifted, and 24 hours after incubation, a single blue-shifted population remained; Panel B is an illustration of exemplary center wavelengths of SWCNTs emission ROIs overlaid on transmitted light images of the HeLa cells wherein a progressive blue-shifting in individual endosomes was observed; Panel C is an illustration of exemplary microtubule polymerization inhibitor nocodazole prevented blue-shifting, while the steroid U18666A exacerbated blue-shifting of SWCNTs emission in HeLa cells relative to control conditions (mean±SD, n=3 trials); Panel D is an illustration of exemplary overlays of SWCNTs emission over brightfield images (top) and filipin staining (bottom) for the same experimental conditions;

FIG. 3 illustrates various aspects of an exemplary live-cell reporting of Niemann-Pick C disease and its therapeutic reversal in lysosomal storage organelles. Panel A is an illustration of an exemplary (8,6) nanotube in wild-type (WT) fibroblasts exhibited a narrow, red-shifted distribution at the 24 hour time point showing nanotubes incubated in NPC fibroblasts reported both a red population and a broad, blue-shifted population; Panel B is an illustration of an exemplary nanotube emission overlaid on transmitted light images show the spatial distribution of this spectral heterogeneity; Panel C shows (a) the SWCNTs in WT fibroblasts maintained their red-shifted emission over 48 hours, (b) that after 48 hours in NPC fibroblasts, the SWCNTs emission became broad and blue-shifted, and (c) that after 24 hours of treatment with 100 μM HPβCD (48 hours after the experiment began), the SWCNTs population in NPC fibroblasts had red-shifted to near-WT levels; Panel D is an illustration of an exemplary nanotube/transmitted light overlays showing the SWCNTs response and reversal quantitatively and spatially and showing that filipin staining of fixed cells under similar conditions confirms the accumulation of cholesterol in NPC cells without HPβCD; Panel E is an illustration of an exemplary nanotube spectral differences in WT, NPC, and cyclodextrin-treated NPC cells plotted with standard error (mean±SD, n=3);

FIG. 4 illustrates various aspects of detection of lysosomal storage disorders. Panel A illustrates mean nanotube emission from wild-type fibroblasts at 24 hours and 48 hours, from patient-derived NPC1 fibroblasts at 24 hours and 48 hours, and from NPC1 fibroblasts treated with cyclodextrin for 24 hours, 24 hours after nanotube addition; Panel B illustrates histograms of the nanotube emission from single lysosomes at 48 hours, from wild-type fibroblasts, NPC1 and NPC1 cells treated with cyclodextrin for 24 hours; Panel C illustrates mean filipin intensity from WT fibroblasts, NPC1 and NPC1 cells treated with cyclodextrin for 24 hours, at 48 hours after nanotube addition; Panel D illustrates mean emission from nanotubes in WT fibroblasts, NPC1, and NPC1 pretreated with cyclodextrin for 24 hours prior to nanotube addition; Panel E illustrates mean emission from nanotubes in RAW 264.7 macrophages in DMEM+ 10% FBS media, in media with 3 ug/L U18666A, and in media with 10 uM Lalistat; Panel F illustrates the histograms corresponding to Panel E; Panel G illustrates model for nanotube emission shift in normal lysosomes, lysosomes with NPC1 phenotype induced with U18666A, and in lysosomes with Wolman's disease induced with Lalistat (all errors bars are S.E.M. from 3 triplicate experiments).

FIG. 5 illustrates various aspects of single cell kinetics of lipid accumulation. Panel A illustrates RAW macrophages in lipoprotein depleted serum (LPDS), incubated with nanotubes for 3 hours (Ac-LDL (100 ug/mL) and U18666A (3 ug/mL) added at t=0 minutes); Panel B illustrates mean emission from 4 independent time courses and single cell trajectories of lysosomal lipid accumulation (error bars=standard deviation, from 4 independent experiments); Panel C illustrates distribution of time constants from single cells undergoing lysosomal lipid accumulation, fit with a log-normal distribution; Panel D illustrates a scatter plot of the starting nanotube emission wavelength against the time constant for lipid accumulation for 60 single cells.

FIG. 6 illustrates various aspects of spatially and temporally correlating lysosomal lipid content to macrophage differentiation. Panel A illustrates changes in macrophage differentiation markers CD11b and F4/80, and the monocyte marker GR1+ on BMDM differentiating in the presence of CSF1; Panel B illustrates transmitted light and fluorescent image of nanotubes localized within the lysosomes of BMDM; Panel C illustrates hyperspectral image of nanotubes in BMDM at days 3 and 5; Panel D illustrates histogram of the mean nanotube emission from BMDM cells at days 3 and 5; Panel E illustrates hyperspectral image of two BMDM cells at day 3, and their corresponding normalized Simpson's Index; Panel F illustrates scatter plot of normalized Simpson's Index with the mean emission from individual cells.

DETAILED DESCRIPTION

The following detailed description is presented to enable any person skilled in the art to use the present methods and kits. For purposes of explanation, specific nomenclature is set forth to provide a thorough understanding of the present methods and kits. However, it will be apparent to one skilled in the art that these specific details are not required to practice the use of the methods and kits. Descriptions of specific applications are provided only as representative examples. The present methods and kits are not intended to be limited to the embodiments shown, but are to be accorded the widest possible scope consistent with the principles and features disclosed herein.

Headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

One aspect of the application relates to a method of detecting a condition in a subject using single-walled carbon nanotubes (SWCNTs). The method comprises the steps of contacting cells of a subject with SWCNTs, monitoring photoluminescence emitted by SWCNTs internalized into said cells and generating an SWCNT emission profile; comparing the SWCNT emission profile to a control emission profile for the SWCNTs; and determining a likelihood of having said condition in said subject based on a result from said comparing step. In some embodiments, photoluminescence emitted by SWCNTs is monitored by hyperspectral imaging.

Nanotubes

As used herein, the term "single-walled carbon nanotubes (SWCNTs)" refers to allotropes of carbon with a cylindrical nanostructure. Most SWCNTs have a diameter of close to 1 nanometer, with a tube length that can be many millions of times longer. The structure of a SWCNT can be conceptualized by wrapping a one-atom-thick layer of graphite called graphene into a seamless cylinder. The way the graphene sheet is wrapped is represented by a pair of indices (n,m). The integers n and m denote the number of unit vectors along two directions in the honeycomb crystal lattice of graphene. If m=0, the nanotubes are called zigzag nanotubes, and if n=m, the nanotubes are called armchair nanotubes. Otherwise, they are called chiral nanotubes. SWCNTs are an important variety of carbon nanotube because most of their properties change significantly with the (n,m) values, and this dependence is non-monotonic. In particular, their band gap can vary from zero to about 2 eV and their electrical conductivity can show metallic or semiconducting behavior. For a given (n,m) nanotube, if n=m, the nanotube is typically metallic; if n–m is a multiple of 3, then the nanotube is typically semiconducting with a very small band gap, otherwise the nanotube is typically a moderate semiconductor. Carbon nanotubes are available from a variety of manufacturers, and may be obtained as sets of unpurified nanotubes within which there are a variety of distinct species present.

In some embodiments, the SWCNTs are semiconducting SWCNTs. Semiconducting SWCNTs exhibit intrinsic photoluminescence which is narrow-band and uniquely photostable. The intrinsic photoluminescence of semiconducting SWCNTs are sensitive to changes in the local dielectric environment, which may result in intensity modulation as well as wavelength shifting (i.e. solvatochromism) of the photoluminescence profile of the semiconducting SWCNTs. The instant application utilizes spatial measurement of the spectral diversity and response of semiconducting SWCNTs in complex biological environments to determine the presence or absence of certain diseased conditions. In some embodiments, the SWCNTs have chiral indices of (6,5) or (8,6).

The SWCNTs may be a mixture of SWCNTs with different chiral indices. In some embodiments, the SWCNTs are a mixture of 2, 3, 4, 5, 6, 7, 8, 9, 10, 11, 12, 13, 14, 15 or more SWCNT species of different chiral indices. In other embodiments, purified or partially purified SWCNT species is used. In some embodiments, the SWCNTs have chiral indices of (8,6) or (6,5).

In some embodiments, the SWCNTs of the present application have an average diameter of 0.1-2 nm, 0.3-1.6 nm or 0.6-1.3 nm. In some embodiments, the SWCNTs of the present application produce fluorescence with a wavelength between about 400-1800 nm, 600-1600 nm, 900-1500 nm, or 1000-1200 nm in an appropriate endocytic dielectric environment. In some embodiments, fluorescence within the claimed ranges is produced using excitation light in the wavelength range of 700-900 nm. In some embodiments, the excitation light has a wavelength of about 730 nm. is detected with wavelength between about 730-880 nm. In some embodiments, a specialized detector is used for fluorescent light with wavelength above 1050 nm.

Nanotubes are not water-soluble, and need to be solubilized or suspended to facilitate intake by cells. In some embodiments, SWCNTs are encapsulated with oligonucleotides (such as single stranded DNA) or synthetic polymers (such as polycarbodiimide or other amphiphilic polymers). Lipids and surfactants may all be used to create a stable suspension of nanotubes. Solubilization/suspension of nanotubes occurs by mixing the chosen encapsulating agent, such as an oligonucleotide or a synthetic polymer, with the nanotube in a weight ratio ranging from 1:1 to 4:1, followed with sonication. Sonication may be performed in a variety of ways, including probe tip ultrasonication and the milder bath sonication.

A large range of DNA oligonucleotides, both in terms of length and sequence, can be used to stably suspend nanotubes. In some embodiments, the oligo nucleotides are single stranded (ss) oligo nucleotides with a length of 2-90 nucleotides. In some embodiments, the oligonucleotides have sequences of $ss(TAT)_n$, $ss(AC)_n$, $ss(ACT)_n$ and $ss(GT)_n$, with n=2-40. In some embodiments, the oligos are $ss(GT)_6$, $ss(GT)_{15}$, $ss(ACT)_6$ or $ss(TAT)_4$, $ss(TAT)_{15}$. In some embodiments, the oligo nucleotides are double stranded oligo nucleotides. In other embodiments, SWCNTs are suspended in detergents, such as sodium deoxycholate (SDC), sodium cholate (SC), sodium dodecylbenzene sulfonate (SDBS) or sodium dodecyl sulfate (SDS). In some embodiments, SWCNTs are encapsulated with oligonucleotides by sonication with oligonucleotides in a buffer solution, such as phosphate buffered saline (PBS). In some embodiments, the SWCNTs are $ss(GT)_6$ encapsulated (8,6) SWCNTs (also referred to as "$ss(GT)_6$-(8,6) nanotubes") or $ss(GT)_6$ encapsulated (6,5) SWCNTs (also referred to as "$ss(GT)_6$-(6,5) nanotubes").

Certain nanotube species are better sensors for lipids than others, One of ordinary skill in the art will understand that the present invention is not limited to any one specific chirality. Nanotubes that are encapsulated with short DNA sequences are preferred for detection of lipids within a particular biological environment. One of ordinary skill will understand that the (8,6) nanotube has been chosen simply as an non-limiting example. There is no limitation upon the present invention of the nature or complexity of the purification technique used to obtain a particular nanotube species, and any technique which may enable independent control of DNA sequence (such as synthetic biology approaches) and or control of nanotube chirality may be used. There is also no limitation upon the present invention to only pure samples of a particular nanotube species, the present invention may use either mixed or pure samples of polymer-encapsulated carbon nanotubes at the discretion of researchers employing the disclosed technique.

Disease Conditions

The compositions, devices and methods of the present application may be used for the detection of disease conditions such as atherosclerosis, coronary heart diseases, stroke, diabetes, cancer, lysosomal storage disorders, hypercholesterolemia and other diseases linked to elevated lipid and cholesterol content.

The term "lysosomal storage disorder" may refer to any of a group of diseases resulting from abnormal metabolism resulting in accumulation of a substrate, such as glycolipids, in the lysosome. Lysosomal storage disorders are caused by lysosomal dysfunction usually as a consequence of deficiency of a single enzyme required for the metabolism of lipids, glycoproteins or mucopolysaccharides. These diseases include, but are not limited to the following: Pompe Disease, Hurler syndrome (Mucopolysaccharidosis type I; MPS-1), Hunter syndrome (MPS-II), Sanfilippo syndrome A (MPS-IIIA), Sanfilippo syndrome B (MPS-IIIB), Sanfilippo syndrome C (MPS-IIIC), Sanfilippo syndrome D (MPS-IIID), classic Morquio syndrome (MPS-IVA), Morquio B Disease (MPS-IVB), Maroteaux-Lamy syndrome (MPS-VI), Sly syndrome (MPS-VII), Sialidosis (Mucolipidosis type I; ML-I), I-cell Disease (ML-II), Pseudo-Hurler Polydystrophy (ML-III), Schindler Disease/Kanzaki Disease, α-Mannosidosis, β-Mannosidosis, α-Fucosidosis, Aspartylglucosaminuria, Niemann-Pick Disease Type C, Niemann-Pick Disease Type D, Neuronal ceroid lipofuscinoses, Wolman Disease, Acid lipase disease, Fabry's Disease, Niemann-Pick-Disease Type A, Niemann-Pick Disease Type B, Gaucher's Disease, Krabbe's Disease, GM1 Gangliosidosis, Tay-Sachs Disease, Sandhoff Disease, Metachromatic Leukodystrophy, Farber Disease, Multiple suifatase deficiency, and Galactosialidosis.

As used herein the term "cancer" refers to any of the various malignant neoplasms characterized by the proliferation of cells that have the capability to invade surrounding tissue and/or metastasize to new colonization sites, including but not limited to carcinomas, sarcomas, melanoma and germ cell tumors. Exemplary cancers include bladder cancer, brain cancer, breast cancer, ovarian cancer, cervix cancer, colon cancer, head and neck cancer, kidney cancer, lung cancer, mesothelioma, prostate cancer, stomach cancer and uterus cancer.

As used herein the term "hypercholesterolemia" refers to the presence of high levels of cholesterol in the blood. Cholesterol is a sterol which is precursor of the steroid hormones, bile acids and vitamin D. Elevated levels of LDL-cholesterol is associated with an increased risk of atherosclerosis and coronary heart disease.

As used herein the term "hyperspectral imaging" is a method of imaging spectroscopy that generates a map of a region of interest based on local chemical composition. In hyperspectral imaging, a two-dimensional image is created having a spectral data inherent in each pixel. These stacks of images comprise a "hypercube." It is possible to correlate the spectrum of each pixel with the presence and concentration of various chemical species. This data can then be construed as a "gradient map" of these species in a surface.

A "subject" refers to either a human or non-human animal. Examples of non-human animals include vertebrates, e.g., mammals, such as non-human primates (particularly higher primates), dogs, rodents (e.g., mice, rats, or guinea pigs), pigs and cats, etc. In a preferred embodiment, the subject is a human. A "biological sample" may refer to a tissue, cell, blood or plasma sample from a subject.

Another aspect of the application relates to a method of monitoring the local dielectric environment in a tissue culture using SWCNTs. The method comprises the steps of contacting cells of a tissue culture of a subject with SWCNTs, monitoring photoluminescence emitted by SWCNTs internalized into said cells and generating an SWCNT emission profile; comparing the SWCNT emission profile to a control emission profile for the SWCNTs; and determining that a change in the local dielectric environment has occurred within the cells of the tissue culture because a blue-shift or red-shift is observed in the wavelength of light reflected by the SWCNTs.

As used herein, the term "blue-shift" refers to a decrease in wavelength, with a corresponding increase in frequency, of electromagnetic waves. In visible light, this shifts the color from the red end of the spectrum to the blue end. The term also applies when photons outside the visible spectrum (e.g., X rays and radio waves) are shifted toward shorter wavelengths, as well as to shifts in the de Broglie wavelength of particles. In some embodiments, a "blue-shift" is defined as a decrease of average wavelength or median wavelength of at least 0.01, 0.03, 0.05, 0.07, 0.09, 0.1, 0.3, 0.5, 0.7, 0.9, 1, 2, 3, 4, 5, 6, 7, 8, 9, 10, 11, 12, 13, 14, 15 or 20, 30, 40, 50 nm.

As used herein, the term "red-shift" refers to an increase in wavelength, with a corresponding decrease in frequency, of electromagnetic waves. In visible light, this shifts the color from the blue end of the spectrum to the red end. The term also applies when photons outside the visible spectrum (e.g., X rays and radio waves) are shifted toward longer wavelengths, as well as to shifts in the de Broglie wavelength of particles. In some embodiments, a "red-shift" is defined as an increase of average wavelength or median wavelength of at least 0.01, 0.03, 0.05, 0.07, 0.09, 0.1, 0.3, 0.5, 0.7, 0.9, 1, 2, 3, 4, 5, 6, 7, 8, 9, 10, 11, 12, 13, 14, 15 or 20, 30, 40, 50 nm Control Emission Profile The control emission profile is the emission profile of a given SWCNT or an oligo-encapsulated SWCNT at a predetermined condition. In some embodiments, the control emission profile is the emission profile of an internalized SWCNT or a plurality of internalized SWCNTs in a normal cell or in a cell that is free from a given condition. In other embodiments, the control emission profile is a emission profile obtained at an earlier time point (e.g., prior to exposure to an test agent, or prior to the development of a condition, or prior to the initiation of a treatment regimen) in the same cell or cells.

Method of Detection of a Lysosomal Storage Disorder

In some embodiments, the present disclosure pertains to a method for detecting lysosomal storage disorder by measuring the endocytic dielectric environment in fibroblasts obtained from a subject using SWCNTs encapsulated in a specific short oligonucleotide. A decrease in the dielectric constant of the endosomal environmental was detected via a distinct solvatochromic blue-shift in emission. A spectrometer, fluorometer, plate reader apparatus, or combinations thereof may be employed for the detection of solvatochromic shift. In one specific embodiment, a spectral imaging/hyperspectral microscope is employed.

In one embodiment, the invention is a method of detection of a lysosomal storage disorder comprising: contacting a tissue, cell, blood or plasma sample from a subject with SWCNTs, determining the fluorescence profile of the SWCNTs and comparing the profile to a control profile of the SWCNTs. If exposure to the tissue, cell, blood or plasma results in a solvatochromic blue-shift of the fluorescence profile of the SWCNTs from the control profile, the subject is at risk of the lysosomal storage disorder.

SWCNTs when used as CNORs undergo a shift in their emission wavelength. In particular, when an SWCNT undergoes a shift in emission wavelength when it interacts with lipids in close proximity, including cholesterol and lipoproteins. When in solution, the SWCNTs of the present invention can detect LDL and total lipid content in solution, whole blood, and patient serum with high sensitivity. When on a surface (e.g. immobilized on a surface as part of a device), the SWCNTs of the present invention can detect LDL and total lipid content at low concentrations. When in cells, the SWCNTs can detect lipid accumulation in the endosomes and lysosomes of live cells. In particular, SWCNTs can detect the direct increase in lipid accumulation in lysosomal storage disorders, such as Niemann Pick Type C or Wolman's Disease. The SWCNTs of the present invention can be used as a screening tool in live cells obtained from patients who have cells with lipid accumulation. This provides an alternative to techniques such as filipin staining used for NPC1.

Lysosomal lipid dysfunction, is correlated with a variety of diseases. For example, non-alcoholic fatty liver disorder (NAFLD, NASH, steatosis) has been shown to cause lysosomal lipid dysfunction in hepatocytes, kupffer cells, and stellate cells from human patients. In certain neurological disorders lipid accumulation in the lysosomes is implicated due to autophagy increasing lipid content in the lysosomes, and has been directly implicated in a variety of diseases. In certain instances, onset of atherosclerosis is associated with lipid droplet formation, which occurs via the lysosomal pathway. Accordingly, all these diseases or any other disease that is caused by or correlated with lysosomal lipid accumulation may be detectable by the methods disclosed herein.

Method of Screening for Drugs to Treat Lysosomal Storage Disorders

In another aspect, the instant application utilizes spatial measurement of the spectral diversity and response of semiconducting SWCNTs in complex biological environments to determine the effect of an agent on the local dielectric environment of a cell.

In one embodiment, a method of screening for drugs to treat lysosomal storage disorders comprises the steps of introducing semiconducting SWCNTs into cells obtained from a subject with a lysosomal storage disorder, determining the fluorescence profile of the SWCNTs, exposing the cells to a candidate agent, determining the fluorescence profile of the SWCNTs after exposure to the agent, and identifying the agent as a candidate for treatment of lysosomal storage disorders when the exposure to the agent results in a red-shift of the fluorescence profile of the SWCNTs.

In another embodiment, a method of analyzing the efficacy of treatment of lysosomal storage disorders comprises the steps of introducing semiconducting SWCNTs into cells obtained from a subject with a lysosomal storage disorder at different stages of treatment, determining the fluorescence profile of internalized SWCNTs at different stages of treatment, wherein a red-shift of the fluorescence profile of the SWCNTs during the course of treatment indicates efficacy of the treatment. In some embodiments, the semiconducting SWCNTs are implanted in vivo in the subject and the fluorescence profile of internalized SWCNTs at different stages of treatment is determined in vivo.

The nanotube emissions from solutions or cells in a 96/384 well plate format may be obtained by an appropriately designed instrument. Such an instrument can be used for high throughput screening for drugs that increase or decrease lipid accumulation in the lysosomes. For example, the present invention may be used for detection and screening for phospholipidosis, a condition characterized by cholesterol accumulation in the lysosomes, which is a side effect in human cells and induced by a variety of drugs currently in human use.

Nanotube emissions are also detectable in small animal in vivo models via appropriately designed pre-clinical instruments. In vivo models for disease progression may be assayed via lysosomal lipid accumulation tracked by the techniques disclosed herein. Disease onset for a variety of disorders as discussed herein, and methods of intervention to treat such diseases can be assayed by acquiring the nanotube emissions from animal models over a period of time using the techniques disclosed herein.

The particular design of the instruments for detection of nanotube emissions as disclosed herein is not limiting on the present invention. For example, a hand-held probe, such as a wand-like device, has been used to detect nanotube emissions (and related shifts in emission wavelengths) in animal models and may be used in human patients. Nanotube emission in the near-infra red is preferred for detection through human tissue than emission at other wavelengths.

Kits

Another aspects of the instant application relates to a kit for detecting endocytic dielectric environment. In some embodiments, the kit comprises SWCNTs and oligo nucleotides in an amount sufficient to encapsulate the single-walled carbon nanotubes. In some embodiments, the kit contains SWCNTs encapsulated in oligo nucleotides. In some embodiments, the kit contains $ss(GT)_6$-(8,6) nanotubes.

Another aspect of the instant application relates to oligonucleotide encapsulated SWCNTs. In some embodiments, the oligonucleotide encapsulated SWCNTs are selected from the groups consisting of $ss(GT)_6$-(8,6) SWCNTs, $ss(GT)_6$-(6,5) SWCNTs, $ss(GT)_{15}$-(8,6) SWCNTs, $ss(GT)_{15}$-(6,5) SWCNTs, $ss(ACT)_6$-(8,6) SWCNTs, $ss(ACT)_6$-(6, 5) SWCNTs, ss(TAT)$_4$-(8,6) SWCNTs, ss(TAT)$_4$-(6,5) SWCNTs, ss(TAT)$_{15}$-(8,6) SWCNTs and ss(TAT)$_{15}$-(6,5) SWCNTs. In other embodiments, the oligonucleotide encapsulated SWCNTs are ss(TAT)$_{n\_}$-(8,6) SWCNTs, ss(AC)$_{n\_}$-(8,6) SWCNTs, ss(ACT)$_{n\_}$-(8,6) SWCNTs, ss(GT)$_{n\_}$-(8,6) SWCNTs, ss(TAT)$_{n\_}$-(6,5) SWCNTs, ss(AC)$_{n\_}$-(6,5) SWCNTs, ss(ACT)$_{n\_}$-(6,5) SWCNTs, ss(GT)$_{n\_}$-(6,5) SWCNTs, wherein n is an integer between 2-40.

The description herein is for the purpose of teaching the person of ordinary skill in the art how to practice the present disclosure, and it is not intended to detail all those obvious modifications and variations of it which will become apparent to the skilled worker upon reading the description. The specific embodiments of the present application have been presented for purposes of illustration and description. They are not intended to be exhaustive or to limit the application and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the claims of the present application.

EXAMPLES

Example 1: Materials and Methods

The below materials and methods were used in the examples herein.

Hyperspectral Microscope System Excitation: A continuous wave (CW) 730 nm diode laser with an output power of 1 W was injected into a multimode fiber to produce the excitation source for photoluminescence experiments. To ensure a homogenous illumination over the entire microscope field of view, the excitation beam passed through a custom beam shaping module to produce a top hat intensity profile within 20% variation on the surface of the sample under test. A long pass dichroic mirror with a cut-on wavelength of 880 nm was aligned to reflect the laser into an Olympus IX-71 inverted microscope equipped with a 100× (UAPON100XOTIRF, NA=1.49) oil objective (Olympus, USA).

Hyperspectral Filter Construction: The hyperspectral filter was situated in the system between the long-pass dichroic mirror and the camera. To decrease the amount of photons produced by elastic laser scattering at the surface of the sample, a long-pass filter with cut-on wavelength of 815 nm was placed at the filter optical input. To ensure that the beam entirely passed through the volume Bragg grating (VBG) for filtering, the pupil of the optical system was imaged between two VBG passes by the first tube lens. Non-resonant light passes through a VBG un-diffracted. Only the wavelength that complies with the Bragg condition will resonate with the grating and be diffracted in the direction of the corner cube. The corner cube was situated to reflect the filtered beam onto the VBG for a second pass in order to cancel chromatic dispersion induced by the first pass and to narrow filtered bandwidth to 3.7 nm. The second tube lens formed a spectrally-filtered image on the IR camera sensor.

To acquire the spectrally filtered image at different wavelengths, the corner cube and the VBG were positioned on rotation stages to continuously tune the diffracted wavelength. An automatic wavelength calibration process was designed to guarantee the relation between the angle of the rotation stage and the absolute wavelength of the grating. Using a xenon spectral lamp (Newport 6033), absolute wavelength accuracy of 0.5 nm was obtained.

Hyperspectral Microscope System Camera: A near-infrared hyperspectral fluorescence microscope was constructed by incorporating a volume Bragg grating to spectrally resolve the entire emitted image. A deep-cooled short-wave infrared (SWIR) camera was designed for the hyperspectral system. By scanning the turret-mounted grating with respect to the collimated emission, a continuous stack of 3.7 nm bandwidth images was constructed by a 2D InGaAs camera. A 2D InGaAs sensor array (nIR camera), operational between 900 nm and 1700 nm and with a quantum efficiency superior to 70%, was used. The array, consisting of 320×256 pixels with 30 μm pitch, was coupled with a four-stage TE cooler to keep the sensor operating temperature below 190 K. The full-well capacity of the camera was 168000 electrons in high gain and 3.5 million electrons in low gain with 65 dB S/N ratio and 346 frames per second capability (full frame). The dynamic range was 14 bits and the readout noise was 57 electrons at 346 fps in high gain. Images in the visible (400-700 nm) range were acquired using a QIClick digital CCD camera (Qimaging, Surrey, BC, Canada) attached to a separate port of the microscope. Hyperspectral cubes were acquired from 900=1400 nm for each of the 256×320 pixels, thus providing 81,920 spectra per acquisition.

Hyperspectral Cube Rectification: Each point source produced a collimated beam having a different incident angle on the VBG, as an image is a sum of point sources issued from different positions of the object seen by the microscope objective. Therefore, the angular selectivity of the grating resulted in a gradient in wavelength across the field of view in the dimension parallel to the dispersion axis. The filtered image produced on the InGaAs camera was composed of a series of vertical lines each with a specific wavelength. To obtain a monochromatic image, several frames at contiguous wavelengths must be scanned through in order to retrieve the wavelength of interest for each image. The reconstruction was performed using cubic interpolation on every pixel for each monochromatic image according to the wavelength calibration parameters.

Nanotube Sample Preparation: Standard chemical reagents were purchased from Sigma-Aldrich (St. Louis, Mo., US) and Fisher Scientific (Pittsburgh, Pa., US). Single-walled carbon nanotubes used throughout the study were commercially purchased and produced by the HiPco process (Unidym, Sunnyvale, Calif., US). Aqueous dispersions were created by the probe-tip ultrasonication of (Sonics & Materials, Inc.) 2 mg of the specified oligonucleotide (IDT DNA, Coralville, Iowa) with 1 mg of raw SWCNT in 1 mL of PBS (Gibco) for 30 minutes or 10 seconds at 40% of the maximum amplitude. Following ultrasonication, the dispersions were ultracentrifuged (Sorvall Discovery 90SE) for 30 minutes at 280,000×g. The top ¾ of the resultant supernatant was collected and its concentration was determined with a UV/Vis/nIR spectrophotometer (Jasco, Tokyo, Japan) using the extinction coefficient $A_{910}$=0.02554 L·mg$^{-1}$·cm$^{-1}$. To remove free DNA, 100 kDa Amicon centrifuge filters (Millipore) were used to concentrate and re-suspend the DNA-nanotube complexes.

To obtain near-pure (6,5) or (8,6)-nanotubes, HiPco sample was dispersed with either ss(TAT)$_4$ or ss(GT)$_6$ oligonucleotides, respectively, and purified according to a previously documented procedure (see X. M. Tu, S. Manohar, A. Jagota, M. Zheng, DNA sequence motifs for structure-specific recognition and separation of carbon nanotubes. Nature 460, 250 (Jul. 9, 2009). Briefly, 1 mL of DNA-nanotube solution, after sonication and ultracentrifugation, was fed into a Hydrocell CNT-NS1500 anion-exchange column (Biochrom) and eluted with a linearly increasing salt gradient of NaSCN using an HPLC (Agilent Technologies, CA, US). Sample purity was confirmed with absorption and estimated at 90% (6,5) and 70% for (8,6).

Cell Lines and Cell Culture Procedures: HeLa CCL-2 cells (ATCC, Manassas, Va., US) were grown under standard incubation conditions at 37° C. and 5% $CO_2$ in sterile-filtered DMEM with 10% heat-inactivated FBS, 2.5% HEPES, 1% Glutamine, and 1% Penicillin/Streptomycin (all Gibco). For studies performed with homozygous mutant NPC, compound mutant heterozygote NPC, or wild-type fibroblasts, the cell lines GM18453, GM03123 or GM05659 (Coriell, Camden, N.J., US), respectively, were cultured in MEM with 10% FBS, 2.5% HEPES, and 1% Glutamine. Cells were plated on glass-bottom petri dishes, or lysine-covered glass dishes (MatTek) for fibroblasts. Unpurified SWCNT were incubated at 1 mg/L and separated SWCNT were incubated at 0.25 mg/L in media with cells for 30 minutes at 37° C. Depending on the experiment, cells were imaged immediately, or trypsinized (Gibco) and re-plated on a fresh glass-bottom petri dish followed by hyperspectral imaging.

Experimental Data Acquisition: For glass surface-based measurements, DNA-nanotubes at 1 mg/L, were incubated on a glass-bottom 35 mm petri dish (Mattek) for 10 seconds and immediately withdrawn by pipette. The surface was washed with PBS and fluorescence data were taken with 9 mL of fresh PBS covering the surface. While focusing on the surface, the individual SWCNTs were excited with a 730 nm laser, ~350 mW power at the sample, and wavelength data were taken from 900 to 1400 nm with 4 nm step sizes and 4 s exposure time. Hyperspectral data from blank surfaces were also taken to be used post-processing in background subtraction.

Data from hyperspectral cubes were analyzed by manually selecting fluorescent nanotube spots with 3×3 pixel ROIs. The mean intensity of a region devoid of ROIs was defined as the background signal. Subtracting the background value from each ROI resulted in an approximately zero baseline for the spectrum from each nanotube.

Pharmacological treatments on HeLa cells were performed with Nocodazole (Sigma, 10 µg/mL added after SWCNT incubation) or U18666A (Sigma, 3 µg/mL added 6 hours prior to SWCNT incubation). Fibroblast cells were incubated with hydroxypropyl-β-cyclodextrin (Sigma, 100 µM) 6 hours prior to SWCNT incubation.

Filipin staining was conducted by fixing cells with 1.5% paraformaldehyde in PBS for 20 minutes. Cells were then labeled with 50 µg/mL filipin for 45 minutes. After washing, filipin images were acquired using 350/50 nm excitation and 460/50 nm emission filters with a 400 nm dichroic long-pass filter (Olympus).

AFM imaging was conducted using freshly cleaved mica (Pelco Mica Disc, V1, Ted Pella) treated with an aqueous $MgCl_2$ (0.5 M) solution for 30 seconds. Excess solution was removed and 10 µL aqueous suspension of purified ss(GT)$_6$-SWCNT (~5 mg/L) was deposited onto the mica and allowed to stand for 20 seconds. The mica surface was then rinsed with water two times to remove unbound carbon nanotubes. The mica was then dried under ultrapure nitrogen stream prior to AFM imaging. AFM images were collected using an Asylum MFD-3D-BIO in AC mode using AC240TS tips (Asylum Research). The typical scan size was 2-5 µm; scan lines and points were 512, and the scan rate was 0.5 Hz-1.95 Hz.

Analysis Software: Hyperspectral data and visible data acquisition, as well as cube rectification, were performed using the PhySpec software (Photon etc, Montreal, Canada) that also controls the hyperspectral microscope. Image processing and (region of interest) ROI selection were conducted using ImageJ and FIJI using the Time Series Analyzer plugin and custom macros. Data analysis, curve fitting, and simulation programs were written in Matlab 2011 (The MathWorks, MA, US). Statistical analysis and graphs were generated using OriginPro 8.6 (OriginLab, Northampton, Mass.). AFM images were acquired and processed in IgorPro (Wavemetrics, Oreg., US).

Sodium deoxycholate (SDC)-suspended HiPCO SWCNTs adsorbed onto a glass surface, were imaged in 0.1% SDC. After fitting each nanotube spectrum with a Voigt function, fits with an $R^2$ value of less than 0.8 were rejected from all following analyses. The wavelength emission peak value was divided by the standard deviation of the baseline (not including the emission peak waveform itself) to obtain the SNR for the particular nanotube. A distribution of the SNR for the sample was created to extract statistical parameters.

Sorting the nanotube emission peaks in ascending wavelength order separated individual nanotube species, either by obvious gaps in the wavelength axis or via a k-means clustering algorithm. The exercise resolved 14 (n,m) nanotube species and provided an absolute count of the nanotube population. Separated populations were assigned (n,m) values based on an empirical Kataura plot as follows:

| # | (n, m) | λstart | λend |
|---|--------|--------|------|
| 1 | (8, 3) | 960 | 970 |
| 2 | (6, 5) | 984 | 993 |
| 3 | (7, 5) | 1028 | 1038 |
| 4 | (11, 0) | 1042 | 1054 |
| 5 | (10, 2) | 1059 | 1076 |
| 6 | (9, 4) | 1107 | 1116 |
| 7 | (8, 4) | 1117 | 1125 |
| 8 | (7, 6) | 1129 | 1145 |
| 9 | (12, 1) | 1179 | 1184 |
| 10 | (8, 6) | 1188 | 1195 |
| 11 | (11, 3) | 1206 | 1216 |
| 12 | (10, 3) | 1270 | 1275 |
| 13 | (10, 5) | 1276 | 1282 |
| 14 | (8, 7) | 1284 | 1300 |

The SWCNTs, adsorbed to a glass substrate, was imaged in the presence of DMEM+10% FBS (D10) before 0.1% (sodium deoxycholate) SDC was introduced to the buffer. The mean wavelength of the SWCNTs was 1201.5 nm. Hyperspectral cubes obtained after 10 minutes showed the SWCNTs emission to reach 1190.5 nm. The shifting was reversed to 1199.1 nm on rinsing the surface with water to remove SDC.

As these nanotubes responded to lipoproteins in solution and on a surface, they could be used to detect lipid accumulation in live cells. Nanotubes encapsulated with either ss(GT)$_6$ or ss(GT)$_{15}$ sequences were incubated in media with HeLa cells at 1 mg/L for 30 minutes at 37° C. before being washed and imaged in fresh media. The spectra were analyzed to obtain the peak emission wavelengths of five nanotube species at different time points. Data was reported as a change from the bulk wavelength value (nm) versus time after initial incubation.

Cells were incubated for 30 minutes with 0.25 mg/L of the SWCNTs before rinsing and replacing with fresh media. Hyperspectral imaging was conducted immediately afterwards and 24 hours later.

Nanotubes with fluorophore-labeled Cy3-ss(GT)$_6$ DNA were encapsulated and co-localized with the Cy3 emission with lysotracker to determine that nanotubes remained localized within the endolysosomal pathway. It was confirmed that visible Cy3 emission also remains co-localized with the nIR emission from the nanotubes themselves. At a 2 pM incubation concentration, no effect of the nanotubes on the proliferation or viability of the cells was observed.

Brightfield images of HeLa cells, and fluorescence images of LysoTracker dye (Deep Red LysoTracker (ex/em 647/668 nm)), were obtained using a QIMAGING CCD camera attached to the hyperspectral microscope. Images of nanotube emission in the same cells were obtained using the InGaAs camera on the same microscope. The two cameras had different aspect ratios and pixel sizes, which were scaled to the same final image size and cropped to represent the same sample area. Emission from the SWCNT, (which shows as blue), was localized within the same regions as the emission from Lysotracker (which shows as red).

HeLa cells were incubated with purified (8,6) nanotubes for 30 minutes. Cells were then trypsinized and re-plated onto glass-bottom Petri dishes. A second incubation was performed with (6,5) nanotubes for 30 minutes (24 hours after the initial incubation). The live cells were then imaged over the 900-1400 nm range with the hyperspectral microscope.

In a similar procedure to the experiment with homozygous NPC cells, fibroblasts with the compound heterozygous mutation of the NPC1 gene were plated on a poly-d-lysine-coated glass-bottomed petri-dish and imaged at different time points after an initial 30 minute incubation with the SWCNTs. Histograms of the wavelength distribution profile of the SWCNTs were obtained.

Example 2: Analysis of Nanotube Emission

Figure 1:
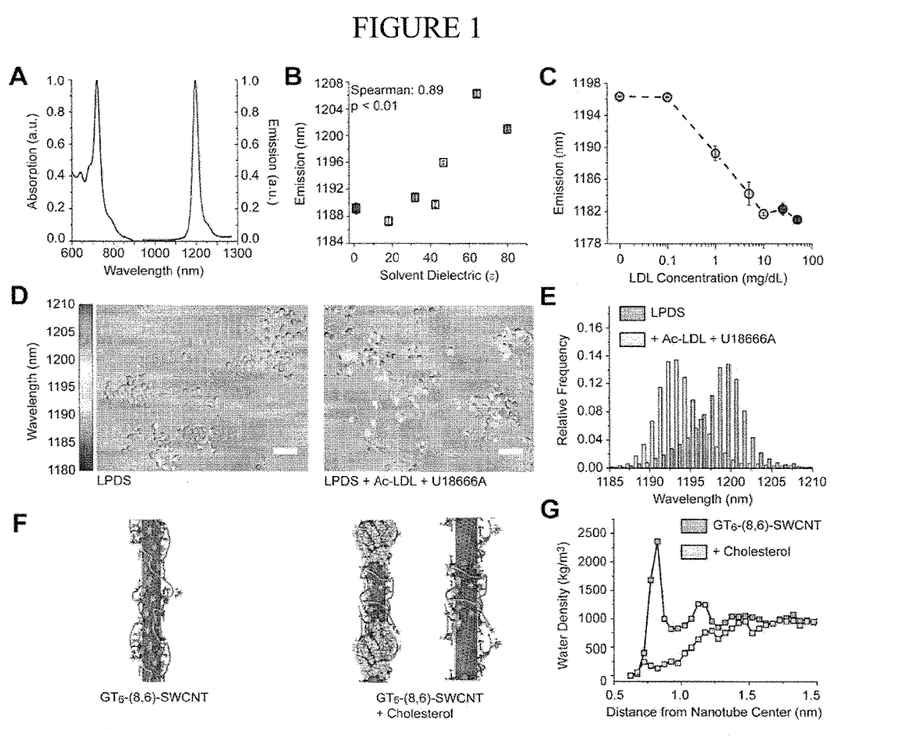

SWCNTs were non-covalently encapsulated in a single stranded oligonucleotide sequence to generate water soluble DNA-nanotube complexes. To test the hypothesis that an optimally short DNA sequence could partially encapsulate the nanotube while leaving enough exposed nanotube surface for hydrophobic molecules to bind to a 12 base long oligonucleotide, GT$_6$, was selected. GT$_6$ also functions as the recognition sequence for the (8,6) chirality. On encapsulating nanotubes with GT$_6$, a mixture of GT$_6$-nanotubes composed of over 15 fluorescent nanotube chiralities were formed. Ion exchange chromatography was performed on this mixture to extract only the (8,6) chirality, so obtaining a pure GT$_6$-(8,6) sample. This GT$_6$-(8,6) sample was free of metallic and carbonaceous impurities, and consisted of a single absorption peak at 730 nm and an emission peak at 1200 nm (FIG. 1, panel A).

Surface adsorbed ss(GT)$_6$-(8,6) nanotubes were dried with ultrapure N$_2$ to remove any associated solution from the nanotube surface. Hyperspectral images from single nanotubes in different solvent environments were acquired to obtain the mean nanotube emission value for each solvent (FIG. 1, panel B). The emission wavelength of ss(GT)$_6$-(8,6) correlated well with the solvent dielectric (Spearman correlation of 0.89, p<0.01)—indicating that as the dielectric value of the environment around the nanotube decreases, the nanotube emission blue shifts.

The ss(GT)$_6$-encapsulated (8,6) nanotubes were introduced to a solution of low density lipoprotein (LDL) to determine if their emission wavelengths respond to whole lipoprotein. The emission shifted monotonically with LDL concentration in solution (FIG. 1, panel C), indicating that the nanotubes were sensitive to this lipid-rich bio-assembly. The response of single nanotubes on a surface to lipids was characterized and the detection of lipidic molecules by the nanotube was found to be immediate and reversible.

Single-walled carbon nanotubes (HiPco), suspended with surfactant and adsorbed onto a glass substrate, were imaged under 730 nm excitation. A hyperspectral cube of nanotube photoluminescence was acquired, spectrally resolving 14 distinct species indicated by their unique chiral indices (n,m). Spectra of individual nanotubes displayed a high signal to noise ratio (average 41.71) and were fit as Voigt profiles to obtain each nanotube's center wavelength, full width at half maximum (FWHM) and intensity. A population analysis of 238 individual nanotubes, using a k-means clustering algorithm, demarcated nanotube species such that their approximate quantities resembled those in the bulk HiPco sample. Analysis of the nanotube emission showed that the FWHM of all species in the 950-1350 nm range fell between 18-23 nm and exhibited a known positive correlation with nanotube wavelength (Pearson's correlation=0.84 with p<0.005). Spectra from DNA-encapsulated (6,5) nanotubes (N=273), separated by ion exchange chromatography, were obtained to determine the intrinsic variability in peak emission wavelength and distribution of FWHMs for a single nanotube (n,m) species. The wavelength distribution centered at 990.22±0.35 nm with an average FWHM of 21.54±0.28 nm.

Example 3: Analysis of Nanotube Localization

Hyperspectral imaging of live HeLa cells incubated with nanotubes resolved 14 distinct internalized (n,m) species. HeLa cells were incubated with 1 mg/L DNA-encapsulated HiPco for 10 minutes and unbound nanotubes were washed away prior to imaging. In agreement with previous studies, the DNA-dispersed nanotubes entered cells via endocytosis and remained in late endosomes and lysosomes. After 30 minutes of incubation, the cells were found to average one photoluminescent nanotube per endosome, measured by counting the number of spatially-resolved emission bands per endosome. Two separated (n,m) nanotube species, were used to label sub-cellular structures. DNA-encapsulated (6,5) nanotubes were imaged 24 hours after internalization within HeLa cells; the nanotubes localized within lysosomes in the perinuclear region. Subsequently, (8,6) nanotubes were imaged immediately after a 30-minute incubation with the same cells, resulting in the localization of these nanotubes within endosomes only. The labeling thus spatially distinguished endosomes and lysosomes by two, narrow near-infrared spectral bands (FWHM~26 nm), separated by 210 nm.

Figure 2:
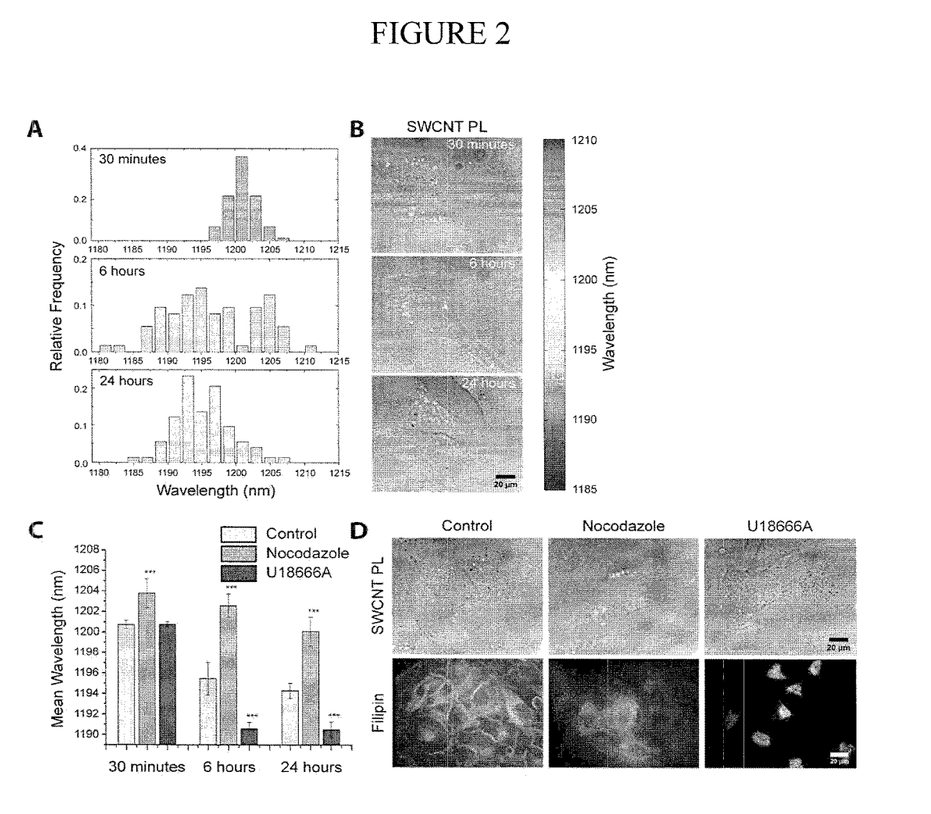

A DNA-encapsulated nanotube complex, undergoing a continuous solvatochromic shifting response, spatially and temporally tracked endosomal maturation in live HeLa cells. Separated (8,6) nanotubes encapsulated by an ss(GT)$_6$ oligonucleotide, with a median length of 236 nm, were incubated with HeLa cells at 0.25 mg/L for 30 minutes before rinsing and replacing with fresh media. The wavelength distribution of the nanotube complex in endosomes, measured immediately after uptake, was centered at 1200.7±0.4 nm, near the bulk value observed in water. In lysosomes, after 6 hours post-incubation, the wavelength distribution broadened before blue-shifting to 1194.3±0.7 nm at the 24-hour timepoint (FIG. 2, panel A). A small red-shifted nanotube population, with a mean wavelength of 1205 nm, appeared at the 6-hour time point but disappeared by 24 hours. The relative mean wavelength of each emissive region of interest (ROI) was laid over a transmitted light image of the cells, resulting in spatial visualization of the spectral distribution (FIG. 2, panel B). Both the inter- and intra-cellular heterogeneity of emission wavelengths progressively increased with endosomal maturation. The nanotube wavelength-shifting phenomenon was found to differ among cell types; MCF-10A epithelial cells caused blueshifting similar to the observation in HeLa cells, nanotubes in RAW 264.7 macrophages exhibited little change relative to bulk nanotubes suspended in water, and GM05659 human fibroblasts produced a red-shifted nanotube population. The interaction of $GT_6$-(8,6) nanotubes with RAW 264.7 macrophages was characterized, by incubating 2 pM of nanotubes in cell media for 30 minutes at 37° C. Under these conditions, the majority of cells efficiently took up nanotubes via energy-dependent mechanisms.

Example 4: Identifying a Carbon Nanotube Optical Reporter of Local Dielectric Environment As nanotube photoluminescence exhibits blue-shifting behavior in lower dielectric environments, the sensitivity of the $ss(GT)_6$ oligonucleotide-encapsulated (8,6) nanotube complex to solvents with known dielectric constants was directly tested. The complex was incubated with butanol ($\varepsilon=18$), resulting in a 14.6±0.9 nm blue shift from the corresponding emission in water ($\varepsilon=80$). In contrast, $ss(TAT)_4$-encapsulated, separated (6,5) nanotube complexes were relatively less sensitive to the local dielectric environment (2.2±0.2 nm blue shift in butanol) and reported negligible wavelength-shifting in live HeLa cells, even at 24 hours. Therefore, the $ss(GT)_6$-(8,6) complex functions as a carbon nanotube optical reporter (CNOR) of local dielectric environment.

Pharmacological inhibition of endosomal maturation by the microtubule polymerization inhibitor nocodazole prevented the blue-shifting of CNOR emission in HeLa cells (FIG. 2, panels C-D). The maturation process of endosomes containing the CNOR by adding nocodazole to the cell media at 10 µg/mL 30 minutes prior to the incubation with the CNOR was halted; these CNORs did not blue-shift for up to 24 hours after internalization (1200.07±1.4 nm mean emission compared to 1194.28±0.73 for control). This result indicates that blue-shifting of the CNOR requires the endosome to lysosome transition and the corresponding change in dielectric environment.

As the CNOR transitions from early endosomes to lysosomes, the environmental pH decreases from pH 6.6 to pH 4.5. To probe the effect of pH on CNOR emission wavelength shifting, $NH_4Cl$—known to increase endosomal pH—was used to alkalinize endocytic organelles in HeLa cells. On addition of 50 mM $NH_4Cl$ to cells 6 hours after incubation with the CNOR, the blue-shifted population remained unaffected while the red-shifted population was depleted. This result, combined with the observed red-shift of the CNOR with lowering pH suggests that the lowering of pH directly causes red-shifting of DNA-nanotube emission but is not responsible for the blue-shifting phenomenon.

The blue-shifting of CNOR emission was enhanced by the drug U18666A, an amphiphilic aminosteroid known to increase the cholesterol content of late endosomes (FIG. 2, panels C-D). HeLa cells treated with 3 µg/mL of the drug for six hours before incubation with the CNOR resulted in a further 3.8±0.7 nm increase in blue shift at 24 hours than in untreated control cells.

A similar effect was observed in RAW 264.7 macrophages; the CNOR exhibited a blue-shift of 11.1±1.1 nm in drug-treated cells relative to a drug-free control. RAW macrophages were incubated in lipoprotein depleted serum (LPDS) for 24 hours. Incubation in these conditions reduces the lipid content of the lysosomes and increases the number of surface receptors for acetylated LDL (Ac-LDL) on the cell surface. To induce lipid accumulation in the lysosomes, Ac-LDL and U18666A (a cholesterol transport inhibitor) were introduced to cells incubating in the lipoprotein depleted serum. After 3 hours of incubation, the combination of Ac-LDL and U18666A results in a significant accumulation of unesterified cholesterol in the lysosomes of treated cells. Nanotubes were added in normal cell media for 30 minutes, before free nanotubes were washed away and the endocytosed nanotubes were given 3 hours to localize to the lysosomes. Hyperspectral images of the nanotubes within cells were acquired, and the images color coded to the peak emission wavelength from each pixel. The hyperspectral images from nanotubes in cells incubated in LPDS were mostly orange and red, while the cells treated with Ac-LDL and U18666A appeared blue and green (FIG. 1, panel D). The histogram of the total nanotube emission from cells in each condition indicates that the nanotube emission from lipid-deficient lysosomes is ~1200 nm while the emission from lipid-rich lysosomes is ~1192 nm (FIG. 1, panel E).

To understand why the accumulation of cholesterol within the constrained volume of a lysosome could induce a blue shift in the emission of the $GT_6$-(8,6) nanotube, all-atom replica exchange molecular dynamics simulations were performed of the nanotube, and the nanotube with cholesterol in its vicinity. The equilibrium configurations obtained after 100 ns indicate that cholesterol partially self-assembles and binds to exposed regions on the nanotube surface. In contrast to the starting configuration, cholesterol also induces rearrangement of DNA on the nanotube surface (FIG. 1, panel F). The net effect of cholesterol binding and DNA rearrangement is a significant decrease in the density of water molecules near nanotube surface (FIG. 1, panel G). Consistent with the shift in nanotube emission due to environmental dielectric (FIG. 1, panel B), displacement of water from the nanotube surface results in a relative blue shift.

Labeling unesterified cholesterol using filipin, which required fixing the cells, displayed a marked qualitative difference between control and drug-exposed cells. In control HeLa cells, filipin strongly illuminated the cholesterol-rich plasma membrane with only a small amount of cholesterol-bound filipin emission appearing from within the cell, while the intensity of filipin in the cell interior increased greatly upon U18666A exposure (FIG. 2, panel D). These results indicate that the CNOR emission undergoes blue-shifting in the presence of endosomal lipids including free cholesterol, the major species up-regulated by the drug.

To confirm the ability of a water-soluble cholesterol derivative to directly affect the emission of the nanotube reporter, the CNOR with sodium deoxycholate (SDC) was probed. The reporter, pre-incubated with cell culture media and serum, was adsorbed to a glass coverslip. A 0.1% solution of SDC was introduced, resulting in an average blue-shift of 11.0±0.7 nm from 1201.5 nm to 1190.5 nm. The blue-shifted CNOR largely reverted back to its initial emission wavelength upon removing SDC. By successively acquiring hyperspectral cubes, the solvatochromic response was found to reach equilibrium in less than 300 seconds. This experiment demonstrates the intrinsic reversibility and rapid response of the reporter to changes in dielectric environment. It suggests that in a cellular environment, the DNA-encapsulated nanotube leaves enough exposed surface such that sterols or other amphipathic molecules can reversibly bind, resulting in an accumulative solvatochromic response to the change in the dielectric environment of the CNOR.

The emission from other (n,m) species in an unsorted ss(GT)$_6$ oligonucotide-encapsulated nanotube sample exhibited similar results to the (8,6) nanotube, with varying degrees of blue-shift observed as a function of time after uptake by HeLa cells. Changing the encapsulating oligonucleotide sequence from ss(GT)$_6$ prevented the blue-shifting phenomenon, indicating sequence-specificity of the optical response. To test whether the CNOR remains intact within the lysosome, ss(GT)$_6$-encapsulated nanotubes was labeled with Cy3 and the organic fluorophore was found to remain quenched by the nanotube surface. This finding confirms the stability of the sensor, as the encapsulating DNA remains associated with the nanotube.

Example 5: Identifying Lysosomal Storage Disorders

Niemann Pick Type-C(NPC) is a lysosomal storage disorder characterized by massive accumulation of unesterified cholesterol in the lysosomes of patient fibroblasts. The solvatochromic shifting of nanotubes clearly distinguished wild-type (WT) fibroblasts from fibroblasts acquired from a patient with NPC. The NPC cells accumulate cholesterol and other lipids within their late endosomes and lysosomes due to a homozygous mutation of the NPC1 gene. At 24 hours after the initial 30 minute incubation with the CNOR, its emission blue-shifted by approximately 10 nm in NPC cells compared to WT fibroblasts (1203.1±0.48 nm for NPC vs. 1209.9±0.32 nm for WT, FIG. 3, panel A). The solvatochromic response was monitored spatially across the cells, showing variations among endosomal compartments (FIG. 3, panel B), but exhibiting clear, quantitative differences between diseased and non-diseased cells (p-value <0.005 for spectral identification of NPC and WT cells).

Figure 3:
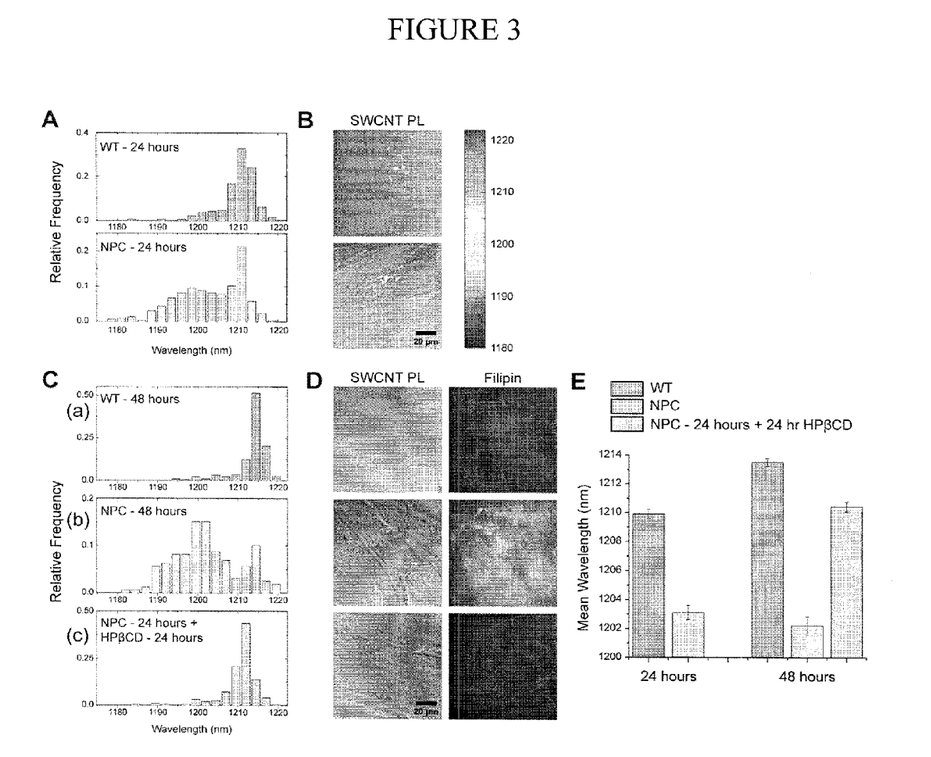

Treatment of homozygous NPC cells with cyclodextrin (HPβCD), a molecule which removes free cholesterol from the lumen of the late endosome/lysosome, caused a reversal of the CNOR blue-shift, thus benchmarking the therapeutic action in live cells. Subsequent to imaging at 24 hours after incubation with nanotubes, NPC fibroblasts were incubated with HPβCD for an additional 24 hours (histograms and overlays in FIG. 3, panels C-D). The effect of HPβCD treatment on CNOR emission from NPC cells was dramatic; the blue-shifted nanotube population transitioned to a red-shifted population and appeared nearly identical to nanotubes in WT cells (FIG. 3, panel E). This result correlated well with staining by filipin, indicating that cyclodextrin removed free cholesterol from the lumen of the late endosome/lysosome, likely driving cholesterol off the nanotube surface and thereby reversing its blue-shifted emission state. Pre-treatment of NPC cells with HPβCD prevented CNOR fluorescence from shifting in diseased cells, resulting in emission that was spectrally identical (p<0.005) to that in WT fibroblasts. Thus, the excess free cholesterol in the late endosome/lysosome of NPC cells is responsible for the blue shift observed when compared to healthy fibroblasts, and removal of the excess free cholesterol inhibits the blue-shift of the CNOR.

Figure 4:
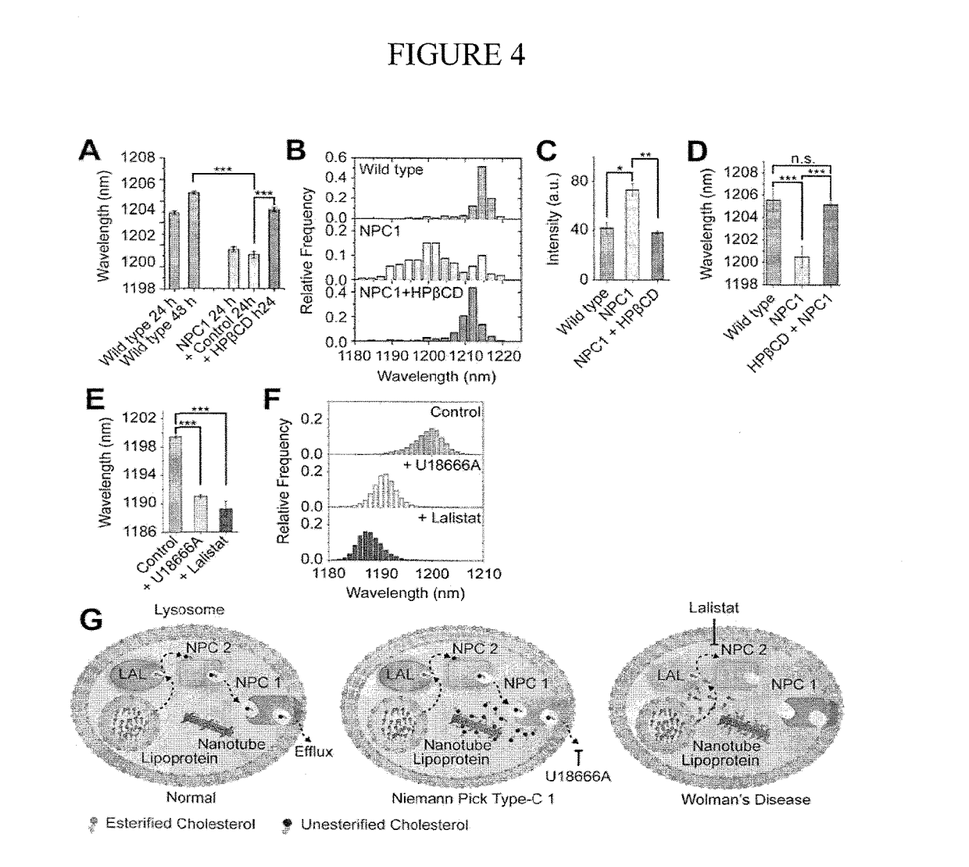

The blue-shifting phenomenon was also demonstrated on fibroblasts from a different patient, with the compound heterozygous mutations of the NPC1 gene, which also exhibit substantial cholesterol accumulation. The lysosomes in NPC1 cells were heterogeneous in their lipid content, in contrast to WT fibroblasts. The reporter was incubated for 30 minutes with cells acquired from a 10-year old patient, before free nanotubes were washed away. Measurements at 24 hours indicated nanotubes in the lysosomes of NPC1 cells to be blue shifted by 6 nm, compared with WT fibroblasts (FIG. 4, panel A). To test the ability of the reporter to detect disease reversal, the NPC1 cells were treated with 100 uM cyclodextrin for 24 hours. This significantly red-shifted the nanotube emisson by approximately 4 nm—and indicated that within the lysosomes of live cells, the reporter is reversible and accurately detected the decrease in cholesterol due to the therapeutic effect of cyclodextrin. By looking at histograms obtained from single lysosomes from cells at 48 hours, WT fibroblast lysosomes were found to be uniformly lipid-poor, with a homogeneous distribution centered at ~1210 nm (FIG. 4, panel B). In contrast, the lysosomes from NPC1 cells showed a broad distribution, and included a lipid-poor fraction, indicating that not all lysosomes demonstrate lipid accumulation. The cyclodextrin treated NPC cells showed a narrow homogeneous distribution of lysosomal lipid content, similar to the distribution observed in WT fibroblasts.

The nanotube results were confirmed by staining the cells with filipin, a fluorescent fixed cell marker with high specificity for cholesterol. Though filipin is not organelle specific, cholesterol accumulation in NPC1 is limited to the lysosomes and thus increased filipin intensity indicates an increase in the cholesterol content of affected lysosomes. Filipin staining confirmed the nanotube emission data as being accurate, with higher filipin intensity observed in blue-shifted cells (FIG. 4, panel C). To confirm that the reporter was specifically detecting cholesterol, NPC1 cells were pre-treated with cyclodextrin. After treatment, the lipid content of these lysosomes should approximate WT cells. Consistent with this finding, nanotubes added to cyclodextrin pretreated cells, and to WT fibroblasts displayed identical emission values, which were significantly red-shifted from untreated NPC1 fibroblasts (FIG. 4, panel D).

The reporter detected Wolman's disease, a lysosomal storage disorder characterized by the accumulation of esterified cholesterol in the lysosomes due to a non-functioning lysosomal acid lipase (LAL). Lalistat, a specific inhibitor of LAL, was used to prevent the hydrolysis of esterified cholesterol. As a positive control in RAW macrophages, the NPC1 phenotype was induced by preventing cholesterol efflux from lysosomes with U18666A. Compared with the control macrophages, both U18666A and Lalistat induced a ~8 nm blue shift (FIG. 4, panel E). Therefore, the reporter blue-shifts due to an accumulation of lipidic molecules in the lysosomes of cells. The lysosomal accumulation of unesterfied cholesterol in NPC1 or esterified cholesterol in Wolman's diseases both result in the binding of lipid molecules to the nanotube surface and induce a blue shift in the nanotube emission (FIG. 4, panel G).

Figure 5:
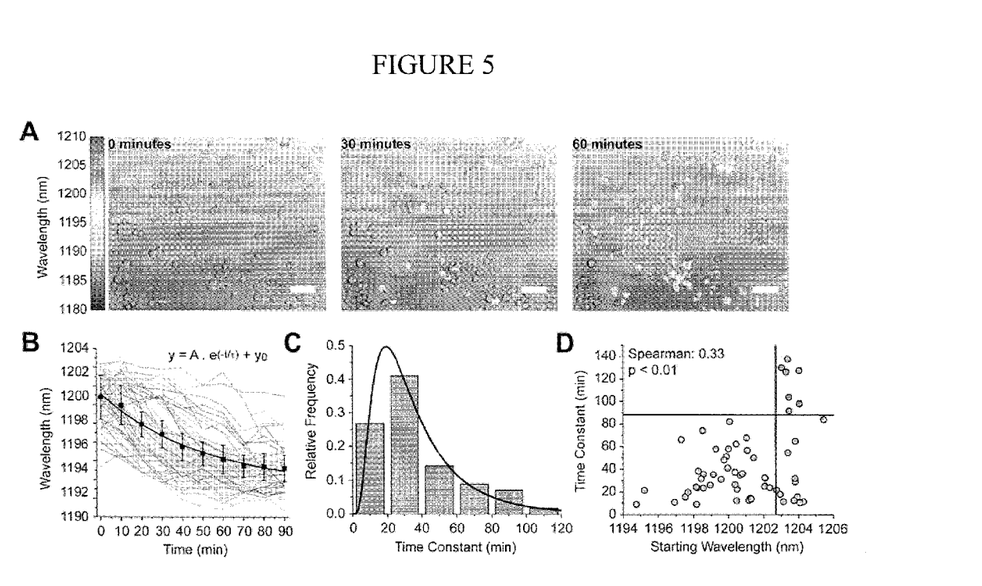

Cells can accumulate lipids within their lysosomes at different rates, and the reporter was used to understand the parameters of lipid accumulation in individual cells. The reporter was localized in the lysosomes of RAW macrophages incubated in lipoprotein depleted serum. The emission from nanotubes in these lipid-poor lysosomes was at ~1200 nm. Upon adding both AcLDL and U18666A to the media, hyperspectral images of the same cells were acquired every 10 minutes for a two hour period. Cells progressively blue shifted due to unesterified cholesterol accumulation within their lysosomes (FIG. 5, panel A). Single cells across hyperspectral images were tracked and the mean nanotube emission from each cell for every time point was extracted. The rate of blue shifting of individual cells can be described as a lag period of no shifting, followed by a single exponential decay. Each single exponential decay can be fit to obtain the time constant for each cell (FIG. 5, panel B)—the average time constant of lipid accumulation is 40 minutes. The distribution of time constants from individual cells follows a log normal distribution, which is consistent with the rate of lipid accumulation within the lysosomes of a single cell being a convolution of multiple independent processes (FIG. 5, panel C). Cells show remarkable heterogeneity in their rate of lipid accumulation, with the slowest and fastest time constants differing by an order of magnitude.

The slowest cells were found to be the ones that started with the most lipid-deficient lysosomes. The time constant of lipid accumulation correlated with the starting wavelength (Spearman correlation of 0.33, $p<0.01$), but interestingly, all slow cells (defined as cells with a time constant greater than 90 minutes) started off with an emission greater than 1202 nm. The time lag before the single exponential blue shifting commenced did not correlate to the starting emission value, the final emission value, the total emission shift or the time constant of decay for single cells. Therefore, cells accumulate lipids in the lysosomes at a rate independent of a lag period preceding lipid accumulation. The rate of lipid accumulation is heterogeneous, and cells slow to accumulate lipids within their lysosomes also start with the most lipid-deficient lysosomes. Lipid accumulation due to U18666A action in the presence of AcLDL uptake is a complex process. Using the reporter directly measures the phenomenon of interest, lysosomal lipid accumulation.

Example 6: Identifying Differentiation State of Bone Marrow

Figure 6:
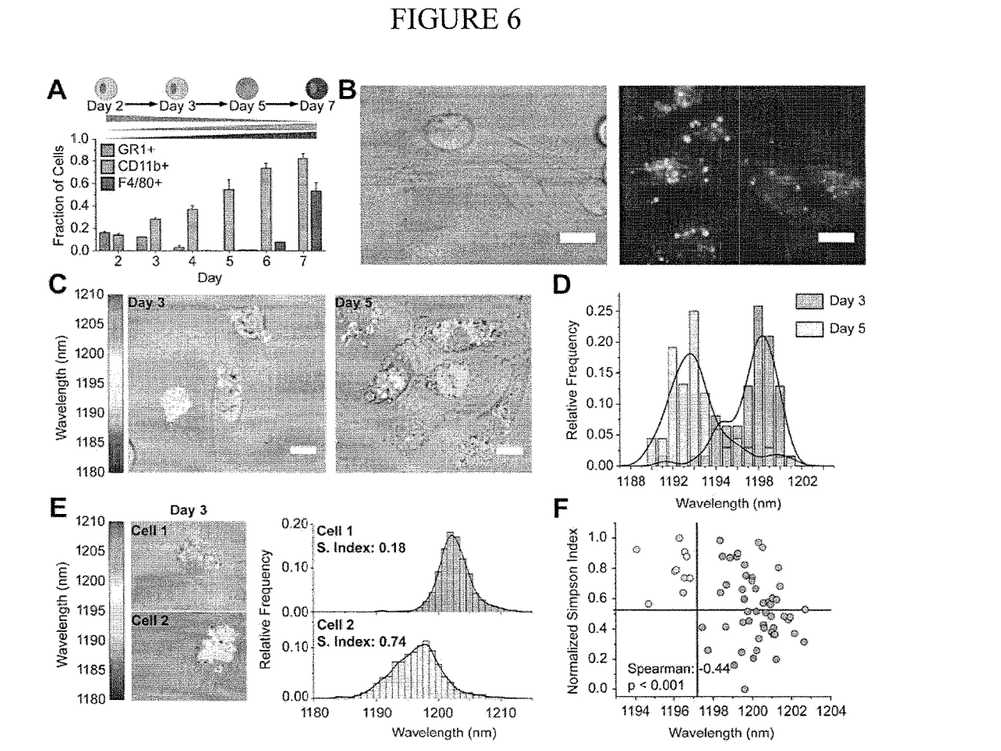

The reporter can correlate lysosomal lipid content with the differentiation state of bone marrow derived macrophages (BMDM). Monocytes in the presence of colony-stimulating factor (CSF1) differentiate into macrophages, as observed by an increase in the fraction of cells expressing the macrophage markers CD11b and F4/80 and a decrease in the fraction of cells expressing the monocyte marker GR1 (FIG. 6, panel A). Nanotubes taken up by BMDM under standard experimental conditions localize in the lysosomes and appear as punctuate spots under 100× magnification (FIG. 6, panel B). Each emissive pixel is fitted to obtain the nanotube emission peak, and thus generates a lysosomal lipid map of individual cells (FIG. 6, panel C). The average nanotube emission from each pixel within a cell gives a mean lysosomal lipid value for that particular cell. A collection of these mean nanotube emission values thus benchmarks a population of cells by the degree of lipid accumulation within their lysosomes. As macrophages differentiate from day 3 to day 5, the nanotube emission significantly blue shifts by ~5 nm (FIG. 6, panel D), indicating that day 5 macrophages have significantly greater lysosome lipid content than day 3 macrophages.

The process of lysosomal lipid accumulation was observed within single cells, by quantifying the intra cellular heterogeneity in lysosomal lipid content. The nanotube emission from lysosomes within a cell was analyzed with two parameters—an average emission value, representing the overall state of lysosomal lipid accumulation within that cell, and a normalized Simpson's Index, to quantify the degree of heterogeneity between lysosomes within that cell. Two typical cells from day 3, showing a relatively homogeneous red cell with a normalized Simpson's Index (nSI) value of 0.18, and a more heterogeneous blue cell with a nSI of 0.74 are shown (FIG. 6, panel E). Plotting the mean emission value of a cell against its nSI demonstrates a clear partitioning, as all blue cells are highly heterogeneous (FIG. 6, panel F). Blue cells being the most heterogeneous indicates that as cells mature and transition from red (lipid deficient lysosomes) to blue (lipid rich lysosomes), individual lysosomes within a single cell also transition from red to blue, which results in an increase in the heterogeneity (both red and blue lysosomes) observed within single cells. The application of the reporter to study differentiating macrophages informs us that lysosomal lipid content increases as monocytes differentiate into macrophages, and this process is observable at the single cell level.

In summary, the above-described non-photobleaching fluorescent probe, localizes to the lysosome, and reports variations in the lipid content of individual lysosomes within live cells. Spatially localizing the nanotube emission generates a endolysosomal lipid map of a cell, and changes in the lysosomal lipid content can be measured over prolonged periods of time with single cell and single lysosome resolution. This carbon nanotube optical reporter indicates that changes in the lysosomal lipid content can occur both due to dysfunctions such as lysosomal storage disorders and normal cellular processes such as macrophage differentiation.

The invention claimed is:

1. A method of detecting elevated lysosomal lipid content in in vitro HeLa cells using single-walled carbon nanotubes (SWCNTs), comprising:
    contacting the HeLa cells in vitro with SWCNTs, wherein said contacting provides SWCNTs internalized into said cells;
    monitoring photoluminescence emitted by SWCNTs internalized into said cells and generating an SWCNT emission profile;
    wherein elevated lysosomal lipid content is detected upon a blue-shift in the SWCNT emission profile from a control emission profile; and
    wherein the SWCNTs are purified (8,6) SWCNTs encapsulated with $ss(GT)_6$ oligonucleotides.

* * * * *